United States Patent
Jih et al.

(10) Patent No.: US 7,282,606 B2
(45) Date of Patent: Oct. 16, 2007

(54) PROCESS FOR PREPARATION OF TAMSULOSIN AND ITS ARALKYLAMINE DERIVATIVES

(75) Inventors: Ru Hwu Jih, Hsinchu (TW); Shwu Chen Tsay, Taipei (TW); Balaachary Magendran, Hsinchu (TW); Subhasish K. Chakraborty, Hsinchu (TW); Asish R. Das, Hsinchu (TW); Kuen Wang Sheu, Taoyuan (TW); Chun Mei Shu, Taoyuan (TW); Chin Kun Lu, Taoyuan (TW); Wei Min Chang, Taoyuan (TW)

(73) Assignees: Well-Being Biochemical Corp., Taipei (TW); Taiwan Biotech Co., Ltd., Tao Yuan Hsien (TW)

( * ) Notice: Subject to any disclaimer, the term of this patent is extended or adjusted under 35 U.S.C. 154(b) by 0 days.

(21) Appl. No.: 11/179,568

(22) Filed: Jul. 13, 2005

(65) Prior Publication Data

US 2007/0015939 A1    Jan. 18, 2007

(51) Int. Cl.
   *C07C 307/10* (2006.01)
(52) U.S. Cl. .......................... 564/80; 564/84
(58) Field of Classification Search ............ None
   See application file for complete search history.

(56) References Cited

U.S. PATENT DOCUMENTS

2006/0036113 A1* 2/2006 Xie .............................. 564/80

FOREIGN PATENT DOCUMENTS

WO    WO2004/087623    * 10/2004

* cited by examiner

*Primary Examiner*—Sikarl A. Witherspoon
(74) *Attorney, Agent, or Firm*—Rosenberg, Klein & Lee

(57) ABSTRACT

The present invention discloses a new process for the synthesis of tamsulosin and its aralkylamine derivatives, especially (R)-(−)-5-{2-[2-(2-alkoxyphenoxy) ethylamino] propyl}-2-alkoxybenzenesulfonamides having the following formula 1 (where $R^1$ and $R^2$ represent $C_1$-$C_4$ alkyl groups) and their hydrochloride thereof, and other various pharmaceutical used salts.

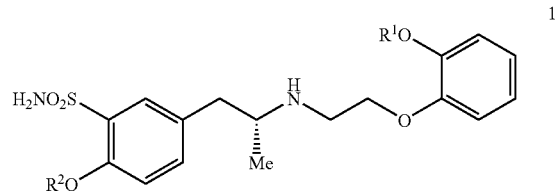

Tamsulosin hydrochloride ($R^1$=Et, $R^2$=Me, in its hydrochloride salt form) is an antagonist of α-A adrenoceptors in the prostate. Tamsulosin•HCl occurs as white crystals, which melt with decomposition at approximately 230° C. It is sparingly soluble in water and in methanol, slightly soluble in glacial acetic acid and in ethanol, and practically insoluble in ether.

4 Claims, No Drawings

PROCESS FOR PREPARATION OF TAMSULOSIN AND ITS ARALKYLAMINE DERIVATIVES

BACKGROUND OF THE INVENTION

1. Field of the Invention

The present invention related to a new process for the preparation of the compounds of the formula 1 (where $R^1$ and $R^2$ represent $C_1$-$C_4$ alkyl group) and their hydrochloride thereof, and other various pharmaceutical used salts. The process is more efficient than the reported processes in total yield and reaction steps for the synthesis of compounds having the formula 1. In the present invention, the use of optically pure starting material can provide the desired compound in more specific range to meet the pharmaceutical requirement. Furthermore, the shorter reaction steps will provide the desired drugs with limit scope of impurity profile.

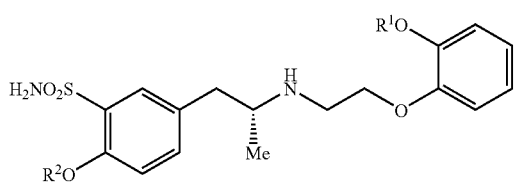

2. Description of the Prior Art

It is described in the U.S. Pat. No. 5,447,958 that the compounds of the above formula 1 have excellent therapeutic effects against hypertension, congestive heart failure, angina pectoris or prostatic hypertrophy. In addition, the above patent disclosed a process for the preparation of compounds with the formula 1 by reacting following hydrochlorides of sulfonamide 2A with bromide 3:

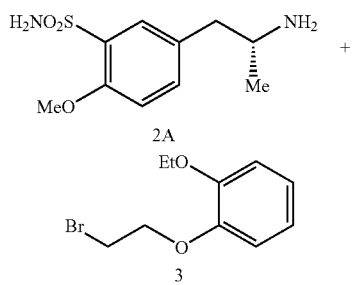

Wherein, sulfonamide hydrochloride salt 2B (hydrochloride of formula 2A) can be synthesized from the Process 1 depicted below. The synthetic procedure of Process 1 involves phenylamine 4A as the starting material to produce the intermediates of acetamide 5A and (sulfo)acetamide 6A, and then to give sulfonamide hydrochloride salt 2B.

Process 1:

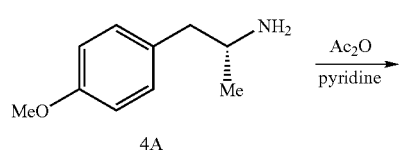

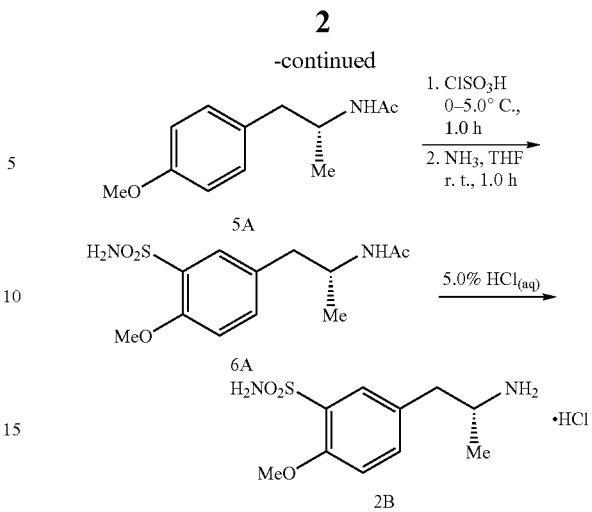

The synthesis of phenylamine 4A was disclosed in U.S. Pat. No. 4,000,197 and *J. Med. Chem.* 1973, 16, 480-483 by condensation of 4-methoxyphenylacetone with (R)-α-methylbenzylamine, followed by hydrogenation of the N=N double bond therein, and reductive debenzylation. The total yield for the preparation of phenylamine 4A is 25% with >99% enantiomeric purity.

Yamada et al. described a process for the synthesis of phenylamine 4A in *Synth. Commun.* 1998, 28, 1935-1945 by using optically pure L-tyrosine as the starting material. The advantage of the current process is that the resultant product is optically pure. The preparation of intermediate 4B (hydrochloride of phenylamine 4A) involves overall 8 steps, and if extended to intermediate 5A, would be 9 steps. Yamada's procedure is depicted in Process 2 as below:

Process 2:

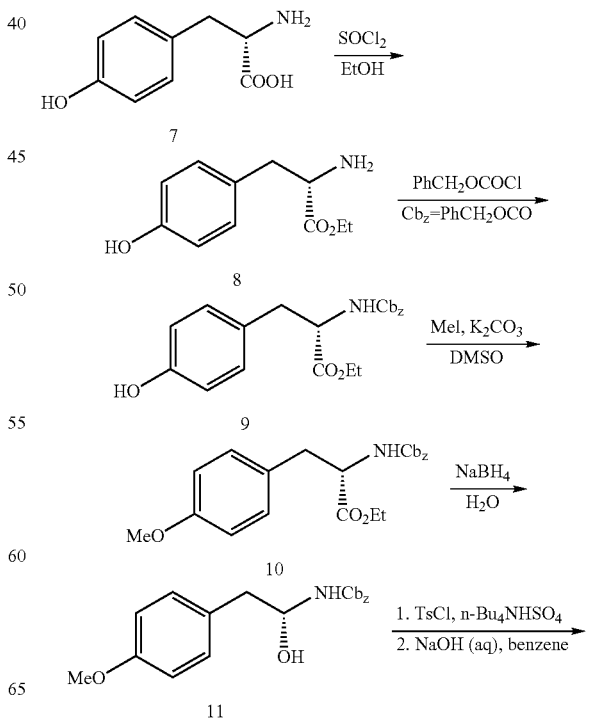

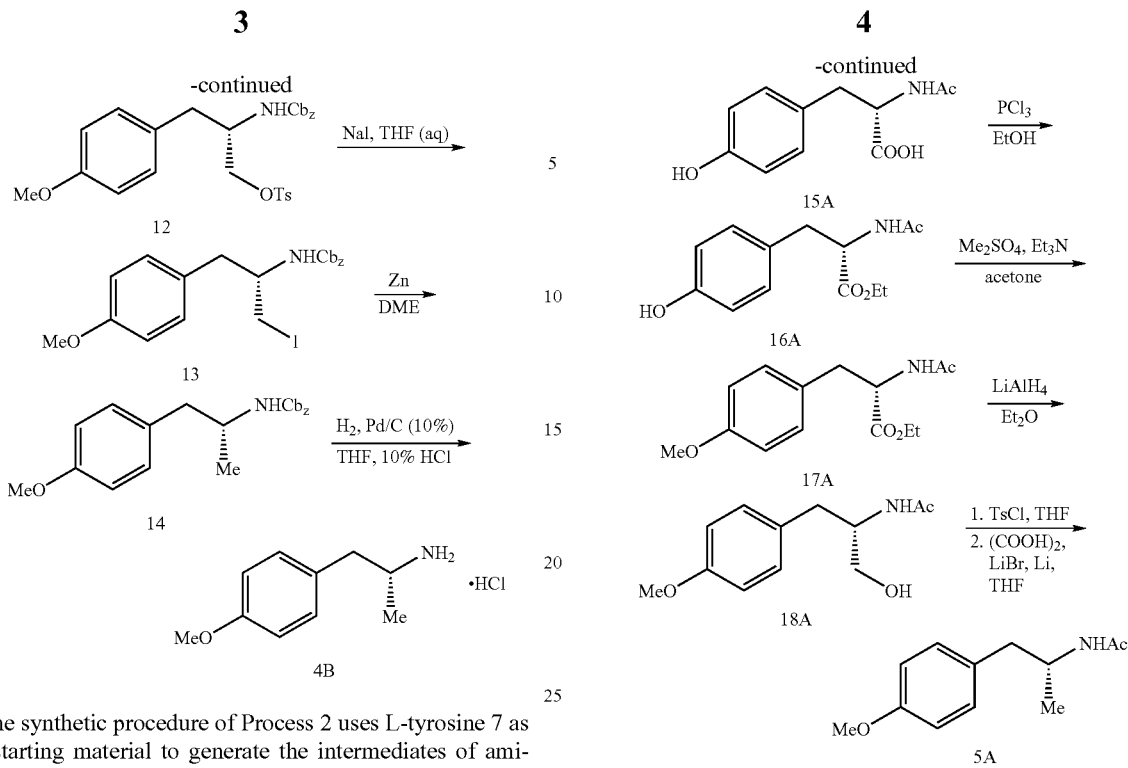

The synthetic procedure of Process 2 uses L-tyrosine 7 as the starting material to generate the intermediates of aminoester 8, (phenol)amidoester 9, (ether)amidoester 10, (hydroxy)ether amide 11, tosyl amide 12, iodide 13, ether amide 14, and finally to obtain hydrochloride of phenylamine 4B.

SUMMARY OF THE INVENTION

The present invention relates to a new process for the synthesis of sulfamoyl-substituted phenoethylamine derivatives and the acidic salts thereof, especially the tamsulosin derivatives having the following formula 1 (where $R^1$ and $R^2$ represent $C_1$-$C_4$ alkyl group) or their hydrochloride thereof, and other various pharmaceutical used salts.

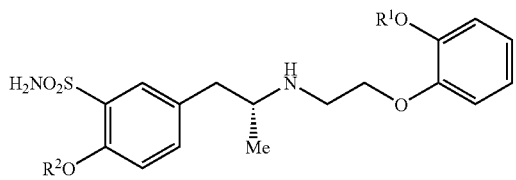

As mentioned before, the synthesis of tamsulosin 1 ($R^1$=Et and $R^2$=Me) involves a key intermediate, i.e. acetamide 5A. Herein, the invention discloses a new process, as shown in Process 3, for the preparation of the key intermediate 5A as depicted below, where comprises the new intermediates, such as (phenol)amido acid 15A, (phenol)amidoester 16A, (ether)amidoester 17A, hydroxy(ether)amide 18A.

Process 3:

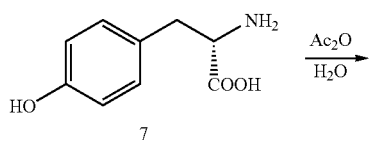

The process is more efficient than the reported processes in total yield and reaction steps for the synthesis of compounds having the formula 1. Furthermore, in the invention, the use of optically pure starting material can provide the desired compound in more specific range to meet the pharmaceutical requirement. And the shorter reaction steps will provide the desired drugs with limit scope of impurity profile.

A new key intermediate (ether)benzoxy tosylate 21A, instead of bromide 3, for the preparation of formula 1 is also disclosed in the invention. It involves the use of 2-ethoxyphenol (19A) as the starting material. Sequential reaction of 19A with chloroethanol and toluenesulfonyl chloride will provide the key intermediate 21A via (ether)benzoxy alcohol 20A. The advantages associated with the use of (ether)benzoxy tosylate 21A instead of bromide 3 will simplify the manipulation of the reaction and, to a more important reason, avoid the pollution resulting from the hazardous halogenated wastes. The process for the preparation of (ether)benzoxy tosylate 21A is depicted as shown in Process 4.

Process 4:

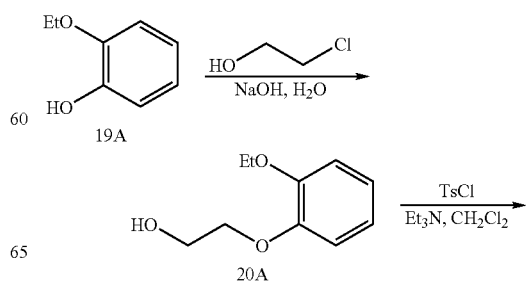

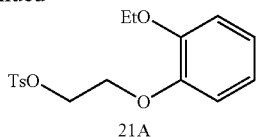

The intermediate acetamide 5A was converted to (sulfo)acetamide 6A and then to sulfonamide hydrochloride salt 2B by the established methods. Sulfonamide hydrochloride salt 2B was allowed to react with (ether)benzoxy tosylate 21A to generate the desired tamsulosin (1, $R^1$=Et, $R^2$=Me). The synthesis of tamsulosin is depicted as shown in Process 5.

Process 5:

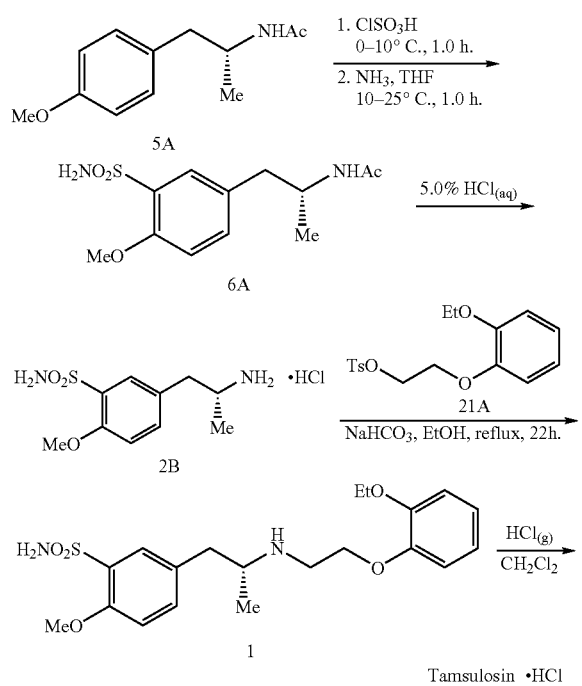

Tamsulosin ·HCl

DESCRIPTION OF THE PREFERRED EMBODIMENTS

The present invention relates to a new process for the synthesis of sulfamoyl-substituted phenoethylamine derivatives and the acidic salts thereof.

A process for the preparation of (phenol)amido acid 15 from starting material L-tyrosine 7 is shown in Process 6.

Process 6:

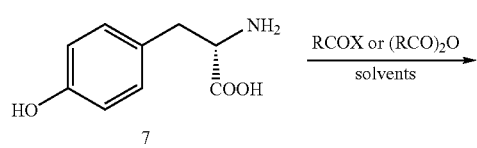

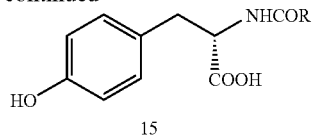

Additionally, an acylating agent and a solvent are used; the acylating agent is selected from RCOX, $(RCO)_2O$ and the combination thereof, wherein R is alkyl or aryl; X is a halide or a leaving group; the solvent is selected from alkanes, ethers, DMF, DMSO, ketones, urea and the combination thereof.

A process for the preparation of (phenol)amidoester 16 from (phenol)amido acid 15 is shown in Process 7.

Process 7:

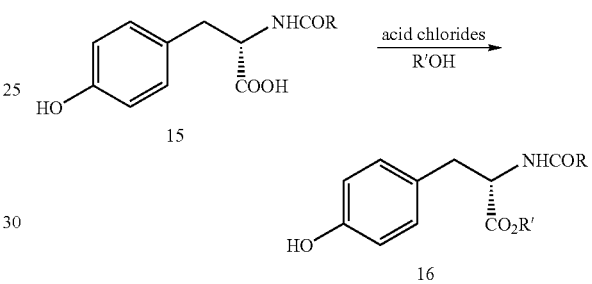

Additionally, an acid chloride and a R'OH are used; the acid chloride is selected from the group of $PCl_3$, $PCl_5$, $POCl_5$, $SOCl_2$, oxalyl chloride and the combination thereof; the R and R' groups are alkyl or aryl.

Furthermore, a process for the preparation of (ether)amidoester 17 from (phenol)amidoester 16 is shown in Process 8.

Process 8:

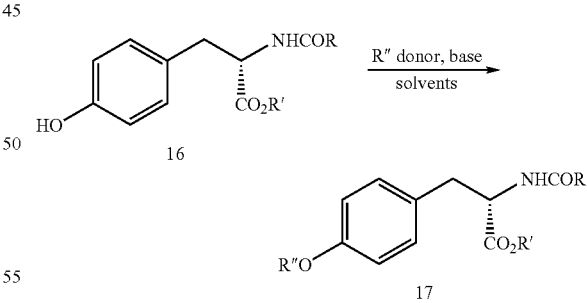

Additionally, an alkylating agent, a base and a solvent are used; the alkylating agent is selected from $R_2SO_4$, RI, RBr and the combination thereof; the base is selected from amines, carbonates, hydrogen carbonates, amides, alkoxides and the combination thereof; the solvent is selected from $H_2O$, ketones, alkanes, ethers, DMF, DMSO, urea and the combination thereof.

A process for the preparation of hydroxy(ether)amide 18 from (ether)amidoester 17 is shown in Process 9.

Process 9:

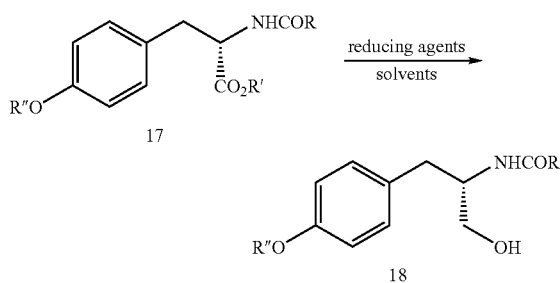

Additionally, a reducing agent and a solvent are used; the reducing agent is selected from LiAlH$_4$, DIBAL, K-selectride, L-selectride, BH$_3$, NaBH$_4$ and the combination thereof; the solvent is selected from ethers, alcohols, H$_2$O, alkanes, DMF, DMSO, urea and the combination thereof.

As shown in Process 10, acetamide 5 can be prepared from hydroxy(ether)amide 18.

Process 10:

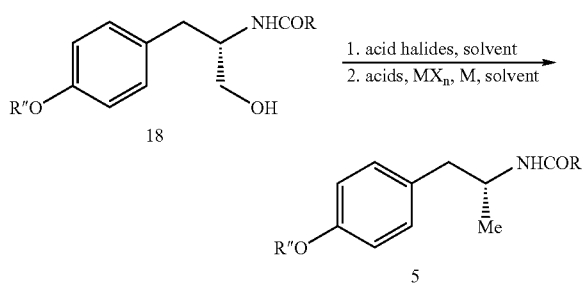

Wherein, an acid halide, a solvent, an organic acid, MXn and M are used; the acid halide is selected from the group of TsCl, MsCl, SOCl$_2$, SO$_2$Cl$_2$, PCl$_3$, PCl$_5$, POCl$_5$, oxalyl chloride and the combination thereof; the solvent is selected from THF, ketones, alkanes, ethers, DMF, DMSO, CH$_2$Cl$_2$, CHCl$_3$, CCl$_4$, urea and the combination thereof, the organic acid is selected from oxalic acid (COOH)$_2$, RCOOH and the combination thereof, where R is H, alkyl, or aryl; the M is selected from Li, Na, K, Mg, Ca, Zn, Pt, Pd, Cu, Co, Mn, Fe, Ni, or Cd; the X is Cl, Br, I, or OAc; the n value is 1-3 based on the valence of the metal.

As mentioned before, the synthesis of tamsulosin 1 involves a key intermediate acetamide 5. Herein, the invention could prepare tamsulosin 1 from acetamide 5.

The present invention can be further understood by the following examples, which are used to illustrate the present invention, but not to limit the scope thereof.

EXAMPLE 1

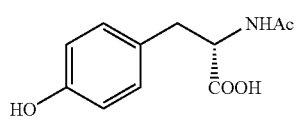

To a solution of L-tyrosine 7 (20.01 g, 110.4 mmol) in H$_2$O (120 mL) was added acetic anhydride (13.51 g, 132.4 mmol). After being heated at reflux for 4.0-5.0 h, the solution was concentrated by distillation to give a light yellow syrupy residue. The residue was dissolved in acetone (80 mL) and the unreacted L-tyrosine 7 was removed by filtration. The filtrate was concentrated under the reduced pressure and the residue was redissolved in ethyl acetate (100 mL), washed with water (50 mL), dried over MgSO$_4$ (s), and concentrated under reduced pressure to obtain (phenol)amido acid 15A (17.62 g, 78.93 mmol) as gel-like semi-solid in 71% crude yield: mp (recrystallized from MeOH) 152-153° C.; specific rotation $[\alpha]_D^{20}$=+ 50.9720°; $^1$H NMR (D$_2$O, 400 MHz) δ 2.07 (s, 3 H, COCH$_3$), 2.82-2.86 (m, 1 H, ArCHH), 2.96-3.01 (m, 1 H, ArCHH), 3.67-3.70 (m, 1 H, CHCOO), 6.70 (d, J=8.0 Hz, 2 H, ArH), 7.01 (d, J=8.0 Hz, 2 H, ArH); IR (neat) 3207 (s), 2961 (m), 1609 (s), 1591 (s), 1513 (s), 1455 (s), 1417 (s), 1363 (s), 1331 (s), 1267 (m), 1245 (s), 1214 (m), 1154 (m), 1112 (m), 1099 (m), 1042 (m), 984 (w), 939 (w), 897 (w), 877 (m), 841 (s), 794 (m), 740 (m), 713 (w), 649 (m), 575 (s), 529 (s), 493 (m), 433 (m) cm$^{-1}$.

EXAMPLE 2

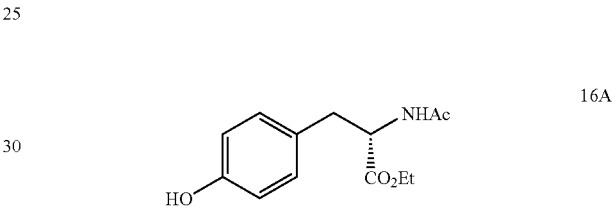

To a solution of (phenol)amido acid 15A (10.01 g, 44.84 mmol) in ethanol (300 mL) was added phosphorus trichloride (18.46 g, 134.4 mmol) dropwisely under ice-salt cooling (5° C.) over a period of 60 min. After being stirred at room temperature overnight, the reaction mixture was concentrated under reduced pressure. The residue was dissolved in ethyl acetate (50 mL), washed with water and saturated aqueous NaHCO$_3$ (25 mL), dried over MgSO$_4$ (s), and concentrated under reduced pressure to obtain (phenol) amidoester 16A (8.225 g, 32.73 mmol) as pale yellow solids in 73% crude yield: mp (recrystallized from 50% EtOAc in hexanes) 126.0-128.0° C.; specific rotation $[\alpha]_D^{20}$=− 1.7632°; $^1$H NMR (CDCl$_3$, 400 MHz) δ 1.24 (t, J=6.8 Hz, 3 H, CH$_2$CH$_3$), 1.97 (s, 3 H, COCH$_3$) 2.95-3.08 (m, 2 H, ArCH$_2$), 4.16 (q, J=6.8 Hz, 2 H, COCH$_2$), 4.79-4.82 (m, 1 H, CHCOO), 6.71 (d, J=8.0 Hz, 2 H, ArH), 6.94 (d, J=8.0 Hz, 2 H, ArH); IR (neat) 3384 (br), 3020 (m), 2927 (m), 2851 (m), 1733 (s), 1652 (s), 1615 (s), 1542 (s), 1516 (s), 1446 (m), 1376 (m), 1219 (s), 1125 (w), 1026 (w), 828 (w), 769 (s), 668 (m), 518 (m) cm$^{-1}$.

EXAMPLE 3

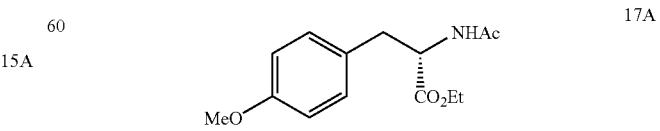

To a solution of (phenol)amidoester 16A (8.021 g, 31.92 mmol) in acetone (35 mL) was added triethylamine (7.365 g, 72.78 mmol) and dimethyl sulfate (5.473 g, 43.39 mmol). After being stirred at 25° C. for 20 h, the solution was quenched with water (50 mL) and extracted with toluene (50 mL). The organic layer was washed with 10% aqueous NaOH (25 mL) and brine (25 mL), dried over MgSO$_4$ (s), filtered, and concentrated under reduced pressure to obtain (ether)amidoester 17A (7.113 g, 26.81 mmol) as light brown semi-solids in 84% crude yield: mp (recrystallized from EtOAc) 140-142° C.; specific rotation $[\alpha]_D^{20}$=−1.6950°; $^1$H NMR (CDCl$_3$, 400 MHz) δ 1.21 (t, J=6.8 Hz, 3 H, CH$_2$CH$_3$), 1.92 (s, 3 H, COCH$_3$), 3.02-3.09 (m, 2 H, ArCH$_2$), 3.95 (s, 3 H, OCH$_3$), 4.14 (q, J=6.8 Hz, 2 H, COCH$_2$), 4.76-4.81 (m, 1 H, CHCOO), 6.76 (d, J=8.0 Hz, 2 H, ArH), 7.02 (d, J=8.0 Hz, 2 H, ArH); IR (neat) 3282 (m), 3075 (w), 2968 (m), 2933 (m), 2837 (w), 1716 (w), 1651 (s), 1614 (s), 1557 (s), 1514 (s), 1456 (s), 1374 (s), 1300 (m), 1248 (s), 1178 (m), 1146 (w), 1114 (w), 1035 (m), 975 (w), 815 (w), 775 (w), 608 (w), 562 (w), 523 (w), 419 (w) cm$^{-1}$.

EXAMPLE 4

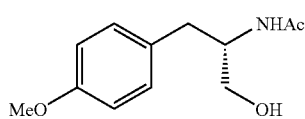

18A

To a stirred solution of LiAlH$_4$ (1.014 g, 26.72 mmol) in diethyl ether (140 mL) was added (ether)amidoester 17A (7.088 g, 26.72 mmol) in diethyl ether (50 mL) under ice water cooling at 10° C. After the solution was stirred at 25° C. for 10 h, the reaction mixture was neutralized with HCl (12 N, 10 mL) and filtered, and the filtrate was concentrated under reduced pressure. The residue was re-dissolved in ethyl acetate (200 mL), washed with water (20 mL), 10% aqueous NaOH (20 mL), brine (20 mL), dried over MgSO$_4$ (s), filtered, and concentrated under reduced pressure to obtain hydroxy(ether)amide 18A (3.579 g, 16.03 mol) as white solids in 60% crude yield: mp (recrystallized from EtOAc and hexanes) 129-130° C.; specific rotation $[\alpha]_D^{20}$=−10.9440°; $^1$H NMR (CDCl$_3$, 400 MHz) δ 1.95 (s, 3 H, NCOCH$_3$), 2.40 (br, 1 H, OH), 2.75-2.85 (m, 2 H, ArCH$_2$), 3.57-3.67 (m, 2 H, CH$_2$O), 3.74 (s, 3 H, OCH$_3$), 4.08-4.14 (m, 1 H, CHN), 6.84 (d, J=8.4 Hz, 2 H, ArH), 7.12 (d, J=8.4 Hz, 2 H, ArH); IR (neat) 3512 (br), 3002 (w), 2948 (m), 2834 (m), 1892 (w), 1645 (s), 1577 (m), 1551 (m), 1511 (s), 1441 (m), 1377 (m), 1300 (s), 1245 (s), 1177 (s), 1083 (m), 1041 (s), 821 (m), 614 (m) cm$^{-1}$.

EXAMPLE 5

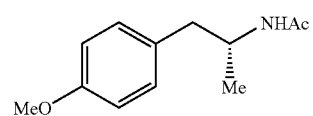

5A

To a solution of hydroxy(ether)amide 18A (10.01 g, 44.83 mmol) in THF (50 mL) was added toluenesulfonyl chloride (15.67 g, 82.19 mmol). After being stirred at reflux for 1.5 h, the reaction mixture was slowly poured into saturated aqueous K$_2$CO$_3$ solution. The aqueous layer was extracted with ethyl acetate (3×20 mL) and the combined organic layer was washed with water (80 mL), dried over MgSO$_4$ (s), and concentrated under reduced pressure. The residue was dissolved in THF (160 mL) containing oxalic acid (20 g) and LiBr (8.118 g, 93.47 mmol) was added. After being stirred at reflux for 10 min, the solution was added with Li (wire, 1.488 g, 214.4 mmol). The resultant solution was stirred at the same temperature for 2.0 h, filtered through celite, washed with ethyl acetate, and concentrated under reduced pressure. The residue was dissolved into water (50 mL), neutralized with K$_2$CO$_3$ (s, 20.01 g), and extracted with ethyl acetate (5×80 mL). The organic layer was washed with water (40 mL) and concentrated under reduced pressure. The residue was added with water (20 mL), kept for overnight, filtered, and dried under vacuum to obtain acetamide 5A (6.711 g, 32.37 mmol) as white solids in 72% crude yield: mp (recrystallized from EtOAc) 90-91° C.; specific rotation $[\alpha]_D^{20}$=+9.9083°; $^1$H NMR (CDCl$_3$, 300 MHz) δ 1.08 (d, J=5.4 Hz, 3 H, CCH$_3$), 1.92 (s, 3 H, COCH$_3$), 2.60-2.77 (m, 2 H, ArCH$_2$), 3.76 (s, 3 H, OCH$_3$), 4.10-4.25 (m, 1 H, CHMe), 6.81 (d, J=7.8 Hz, 2 H, ArH), 7.06 (d, J=7.8 Hz, 2 H, ArH); IR (neat) 3276 (br), 3077 (m), 2969 (m), 2933 (m), 2836 (m), 1716 (m), 1647 (s), 1615 (s), 1542 (s), 1513 (s), 1456 (m), 1374 (m), 1300 (m), 1247 (s), 1178 (m), 1035 (m), 814 (m), 755 (w), 518 (w), 420 (w) cm$^{-1}$.

EXAMPLE 6

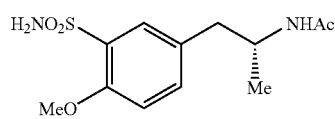

6A

To acetamide 5A (1.01 g, 4.81 mmol) was added chlorosulfonic acid (10.1 g, 85.8 mmol) under cooling at 0-10° C. The solution was stirred at 5.0° C. for 1.0 h. The reaction mixture was slowly poured into ice water and the resultant oily material was extracted with ethyl acetate (100 mL). The organic layer was washed with saturated aqueous NaHCO$_3$ (25 mL), H$_2$O (10 mL), dried over MgSO$_4$ (s), filtered, and concentrated under reduced pressure. The residue was redissolved in THF (20 mL), added with concentrated aqueous ammonia solution (15 N, 30 mL), and stirred at 25° C. for 1.0 h. The solution was concentrated under reduced pressure, and the resultant residue was washed with water (2.0 mL) and dried under reduced pressure to obtain (sulfo) acetamide 6A (602.1 mg, 2.102 mmol) as white solids in 44% crude yield: mp (recrystallized from MeOH) 198-199° C.; specific rotation $[\alpha]_D^{20}$=+13.2634°; $^1$H NMR (D$_2$O, 400 MHz) δ 0.99 (d, J=6.8 Hz, 3 H, CCH$_3$), 1.68 (s, 3 H, COCH$_3$), 2.43-2.49 (m, 1 H, ARCHH), 2.69-2.74 (m, 1 H, ArCHH), 3.72 (s, 3 H, OCH$_3$), 3.80-3.86 (m, 1 H, CHMe), 7.01 (d, J=8.8 Hz, 1 H, ArH), 7.33 (d, J=8.8 Hz, 1 H, ArH), 7.48 (s, 1 H, ArH); IR (neat) 3132 (br), 1654 (s), 1609 (m), 1536 (m), 1496 (m), 1401 (s), 1320 (m), 1283 (m), 1253 (m), 1176 (w), 1148 (s), 1070 (m), 1024 (m), 977 (w), 927 (w), 860 (w), 838 (w), 828 (w), 761 (m), 701 (w), 669 (w), 614 (m), 599 (m), 572 (m), 535 (m), 505 (m), 450 (m) cm$^{-1}$; ESI-MS m/z 287.27 (M+H$^+$).

EXAMPLE 7

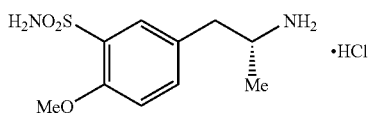

An aqueous HCl solution (5.0%, 25 mL) containing (sulfo)acetamide 6A (0.541 g, 1.88 mmol) was heated at reflux for 16 h. The solution was concentrated under reduced pressure, redissolved in hot MeOH (3.0 mL), and slowly added with ethyl acetate (10 mL). The precipitate was collected and dried under vacuum to obtain sulfonamide hydrochloride salt 2B (0.449 g, 1.60 mmol) as white solids in 85% yield: mp (recrystallized from MeOH) 272-273° C. (dec.); specific rotation $[\alpha]_D^{20}$=−9.2040°; $^1$H NMR (D$_2$O, 400 MHz) δ 1.14 (d, J=6.4 Hz, 3 H, CCH$_3$), 2.79-2.82 (m, 2 H, ArCH$_2$), 3.43-3.56 (m, 1 H, CHMe), 3.84 (s, 3 H, OCH$_3$), 7.10 (d, J=8.4 Hz, 1 H, ArH), 7.42 (d, J=8.4 Hz, 1 H, ArH), 7.58 (s, 1 H, ArH); IR (neat) 3329 (s), 3196 (s), 3150 (s), 3025 (s), 2944 (s), 2701 (w), 2590 (w), 2501 (w), 1611 (m), 1553 (m), 1496 (s), 1402 (s), 1327 (s), 1282 (m), 1255 (m), 1154 (s), 1075 (m), 1017 (m), 928 (m), 828 (w), 804 (m), 703 (m), 601 (s), 572 (m), 536 (m), 507 (m) cm$^{-1}$; ESI-MS m/z 245.15 (M+H$^+$); Anal. Calcd for C$_{10}$H$_{17}$N$_2$O$_3$SCl: C, 42.78; H, 6.10; N, 9.98. Found: C, 42.76; H, 6.15; N, 9.93.

EXAMPLE 8

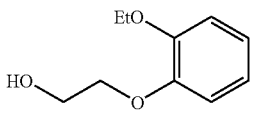

To a solution of 2-ethoxyphenol 19A (13.82 g, 100.1 mmol) in aqueous NaOH (1.0 N, 300 mL) was added chloroethanol (33.12 mL, 500.1 mmol). After being stirred at 25° C. for 48 h, the reaction mixture was extracted with ethyl acetate (3×100 mL). The organic layer was dried over MgSO$_4$ (s), filtered, and concentrated under reduced pressure to obtain (ether)benzoxy alcohol 20A (14.02 g, 76.94 mmol) as yellow liquid in 77% yield: $^1$H NMR (CDCl$_3$, 400 MHz) δ 1.44 (t, J=7.2 Hz, 3 H, OCH$_2$CH$_3$), 3.85 (t, J=7.2 Hz, 2 H, CH$_2$OH), 4.05-4.12 (m, 4 H, OCH$_2$CH$_3$+OCH$_2$CH$_2$OH), 6.88-6.97 (m, 4 H, ArH); IR (neat) 3547 (br), 3066 (m), 2977 (s), 2931 (s), 2877 (s), 1739 (m), 1649 (m), 1593 (s), 1503 (s), 1455 (s), 1393 (m), 1324 (m), 1253 (s), 1219 (s), 1123 (s), 1041 (s), 922 (s) cm$^{-1}$

EXAMPLE 9

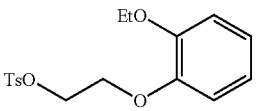

To a solution of (ether)benzoxy alcohol 20A (501.2 mg, 2.751 mmol) in CH$_2$Cl$_2$ (20 mL) was added Et$_3$N (509 mg, 5.03 mmol) and toluenesulfonyl chloride (623 mg, 3.27 mmol) at 5-10° C. After being stirred at 25° C. for 30 min, the reaction mixture was quenched with saturated aqueous Na$_2$CO$_3$ (20 mL) and extracted with ethyl acetate (3×50 mL). The combined organic layers were dried over MgSO$_4$ (s), filtered, and concentrated under reduced pressure to obtain (ether)benzoxy tosylate 21A (853.5 mg, 2.539 mmol) as white solids in 92% yield: mp (recrystallized from CH$_2$Cl$_2$ and CCl$_4$) 82-83° C.; $^1$H NMR (CDCl$_3$, 300 MHz) δ 1.43 (t, J=10.2 Hz, 3 H, OCH$_2$CH$_3$), 2.51 (s, 3 H, ArCH$_3$), 4.04 (q, J=10.2 Hz, 2 H, OCH$_2$CH$_3$), 4.36 (t, J=6.9 Hz, 2 H, OCH$_2$CH$_2$), 4.59 (t, J=6.9 Hz, 2 H, OCH$_2$CH$_2$), 6.86-6.97 (m, 4 H, ArH), 7.10-7.22 (m, 4 H, ArH); IR (neat) 3446 (br), 2982 (m), 2934 (m), 2884 (m), 1591 (s), 1558 (w), 1509 (s), 1478 (s), 1454 (s), 1407 (s), 1394 (s), 1371 (s), 1354 (s), 1279 (m), 1259 (s), 1247 (s), 1217 (s), 1178 (s), 1127 (s), 1066 (s), 1043 (s), 1031 (s), 977 (s), 929 (s), 905 (s), 809 (s), 776 (m), 749 (s), 776 (m) cm$^{-1}$

EXAMPLE 10

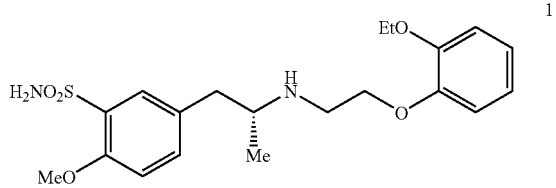

To a solution of sulfonamide hydrochloride salt 2B (1.12 g, 4.00 mmol) in EtOH (40 mL) was added NaHCO$_3$ (672 mg, 8.00 mmol). After being stirred at room temperature for 5.0 min, the solution was added with (ether)benzoxy tosylate 21A (1.34 g, 4.00 mmol). The solution was stirred at 90-100° C. for 22 h. The reaction mixture was cooled to room temperature, filtered, concentrated under reduced pressure, and dried under vacuum. The resultant semi-solid was dissolved in CH$_2$Cl$_2$ (50 mL), filtered, and the solid was washed with CH$_2$Cl$_2$ (3×5.0 mL). The residual solid was recovered as the unreacted sulfonamide 2A. The filtrate was concentrated under reduced pressure, and the residue was dissolved in CHCl$_3$ (50 mL) and washed with water (3×25 mL). The aqueous solution was added with brine and then extracted with EtOAc to obtain the unreacted sulfonamide 2A. The organic layer was dried over MgSO$_4$ (s), filtered, and concentrated under reduced pressure. The residue was dried under vacuum and the solid was washed with CCl$_4$ (3×20 mL). Ethoxyphenol 19 was recovered by concentration of the CCl$_4$ solution. The solid was purified by column chromatography on silica gel (37% MeOH in CHCl$_3$ as eluant) to obtain tamsulosin 1 (571 mg, 1.40 mmol) as white solids in 35% yield: mp (recrystallized from CH$_2$Cl$_2$ and EtOAc) 129-131° C.; specific rotation $[\alpha]_D^{20}$=−14.7240°; $^1$H NMR (CD$_3$OD, 400 MHz) δ 0.99 (d, J=6.4 Hz, 3 H, NCHCH$_3$), 1.28 (t, J=7.2 Hz, 3 H, OCH$_2$CH$_3$), 2.49-2.54 (m, 1 H, ArCHH), 2.77-2.82 (m, 1 H, ArCHH), 2.89-2.98 (m, 3H, NCH$_2$+NCH), 3.88 (s, 3 H, OCH$_3$), 3.93-4.57 (m, 4 H, CH$_2$CH$_2$O+CH$_3$CH$_2$O), 6.81-6.89 (m, 4H, ArH), 7.03 (d, J=8.4 Hz, 1 H, ArH), 7.36 (d, J=8.4 Hz, 1 H, ArH), 7.63

(s, 1 H, ArH); IR (neat) 3284 (m), 2973 (m), 2939 (m), 1592 (m), 1504 (s), 1442 (m), 1324 (s), 1282 (m), 1249 (s), 1214 (m), 1154 (s), 1125 (m), 1073 (m), 1046 (m), 971 (w), 925 (m), 753 (m) cm$^{-1}$; ESI-MS m/z 409.40 (M+H$^+$).

EXAMPLE 11

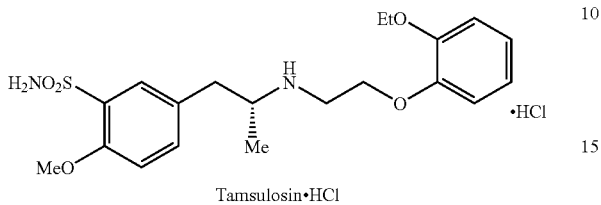

Tamsulosin•HCl

To a solution of tamsulosin 1 (2.011 g, 4.917 mmol) in CH$_2$Cl$_2$ (50 mL) was bubbled with excess dry HCl$_{(g)}$ at 0-5° C. for 1.0 h. The resultant precipitate was filtered and dried under vacuum at room temperature to obtain tamsulosin•HCl (2.091 g, 4.699 mmol) as white solids in 96% yield: mp (recrystallized from 50% MeOH in EtOH) 230-231° C.; specific rotation $[\alpha]_D^{20}$=−5.3843°; $^1$H NMR (D$_2$O, 400 MHz) δ 1.14-1.17 (m, 6 H, NCHCH$_3$+OCH$_2$CH$_3$), 2.71-2.76 (m, 1 H, ArCHH), 2.95-3.00 (m, 1 H, ArCHH), 3.36-3.43 (m, 2 H, NCH$_2$), 3.53-3.55 (m, 1 H, NCH), 3.75 (s, 3 H, OCH$_3$), 3.94-3.97 (m, 2 H, MeCH$_2$O), 4.04-4.19 (m, 2 H, OCH$_2$CH$_2$), 6.84-6.96 (m, 5 H, ArH), 7.35 (d, J=8.8 Hz, 1 H, ArH), 7.54 (s, 1 H, ArH); IR (neat) 3304 (m), 3168 (m), 2981 (m), 1610 (m), 1589 (m), 1500 (s), 1458 (m), 1392 (m), 1339 (s), 1251 (s), 1215 (s), 1160 (s), 1128 (s), 1072 (m), 1046 (m), 1018 (m), 820 (m), 749 (s), 718 (m) cm$^{-1}$.

In the present invention a process for preparation of tamsulosin and its aralkylamine derivatives is disclosed. The steps for preparation of tamsulosin from starting material L-tyrosine are fewer and the yield is higher than that of the conventional method, meanwhile, the key intermediates 15A to 18A as synthesized during tamsulosin 1 preparation are also representative intermediates for the present invention.

Those embodiments described above are only to clarify the technical contents and characteristics of the present invention so that the persons skilled in the art can understand, make, and use the present invention but not intended to limit the scope of the present invention. Any equivalent modification and variation according to the spirit of the present invention is to be included within the scope of the present invention.

What is claimed is:
1. A process for the preparation of tamsulosin having the following formula 1;

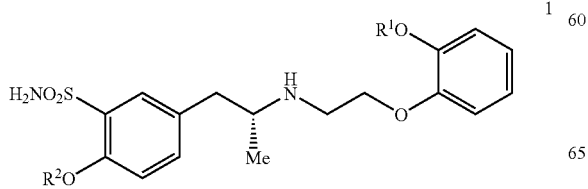

the process comprising the steps of:
reacting the hydrochloride of sulfonamide 2 with the ether compound 21 to obtain the tamsulosin 1;

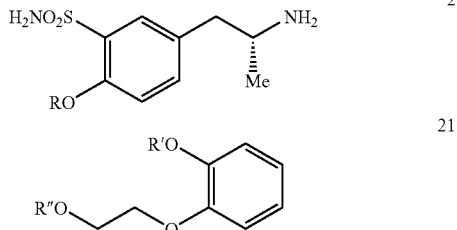

wherein R$^1$ is ethyl and R$^2$ is methyl for tamsulosin 1, R in formula 2 represents Me, as shown by 2A, and the hydrochloride of 2A is shown by 2B; in ether compound 21, R' represents Et and R" represents Ts, as shown by the (ether)benzoxy tosylate 21A;

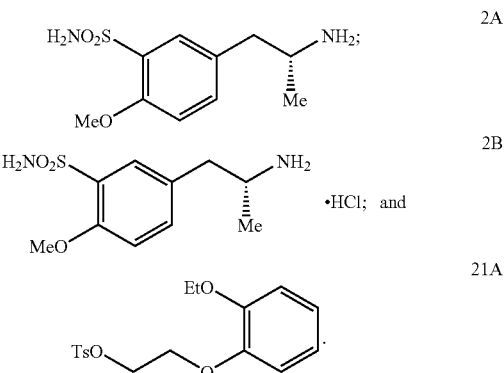

where forming sulfonamide hydrochloride salt 2B is done by converting acetamide 5A to (sulfo)acetamide 6A by reacting said acetamide 5A with:
(a) chlorosulfonic acid: followed by
(b) ammonia in tetrahydrafuran (THF);
followed by obtaining said sulfonamide hydrochloride salt 2B under an aqueous hydrochloride solution;

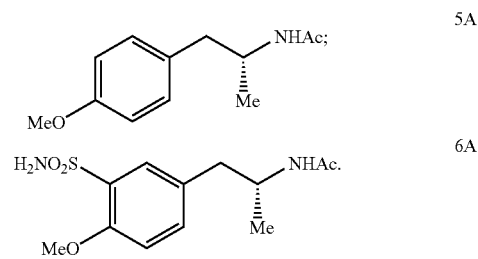

2. The process for the preparation of tamsulosin as claimed in claim 1, wherein the intermediates as shown below are used for preparing acetamide 5;
(1) the (phenol)amido acid 15 having the following formula:

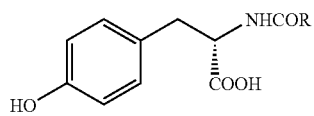

wherein R represents alkyl or aryl;

(2) the (phenol)amidoester 16 having the formula:

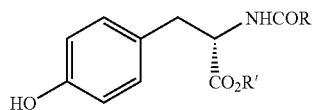

wherein R and R' represent alkyl or aryl;

(3) the (ether)amidoester 17 having the following formula:

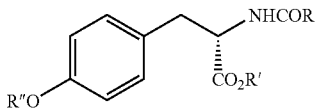

wherein R, R' and R" represent alkyl or aryl; and (4) the hydroxy(ether)amide 18 having the following formula:

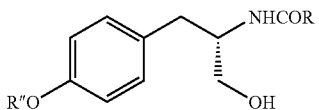

wherein R and R' represent alkyl or aryl.

3. The process for the preparation of tamsulosin as claimed in claim 1, wherein the (ether)benzoxy tosylate 21 (R" represents $MeC_6H_4SO_2$ or $MeSO_2$) is prepared by converting 2-ethoxyphenol 19 to (ether)benzoxy alcohol 20, and then to (ether)benzoxy tosylate 21;

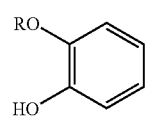

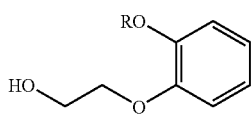

wherein R represents alkyl or aryl.

4. A process for the preparation of tamsulosin having the following formula 1:

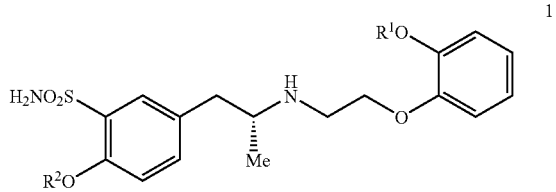

wherein the improvement comprises forming acetamide 5A using L-tyrosine 7, a (phenol)amido acid 15, a (phenol)amidoester 16, an (ether)amidoester 17, and a hydroxy(ether)amide 18 in said process of forming tamsulosin 1, comprising the steps of:

reacting the hydrochloride of sulfonamide 2 with the ether compound 21 to obtain the tamsulosin 1;

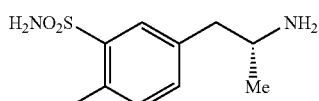

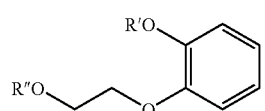

wherein $R^1$ is ethyl and $R^2$ is methyl for tamsulosin 1, R in formula 2 represents Me, as shown by 2A, and the hydrochloride of 2A is shown by 2B; in ether compound 21, R' represents Et and R" represents Ts, as shown by the (ether)benzoxy tosylate 21A;

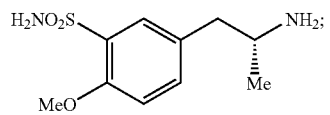

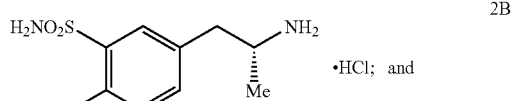

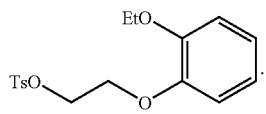

where forming sulfonamide hydrochloride salt 2B is done by converting acetamide 5A to (sulfo)acetamide 6A by reacting said acetamide 5A with;

(a) chlorosulfonic acid; followed by (b) ammonia in tetrahydrafuran (THF);

followed by obtaining said sulfonamide hydrochloride salt 2B under an aqueous hydrochloride solution;

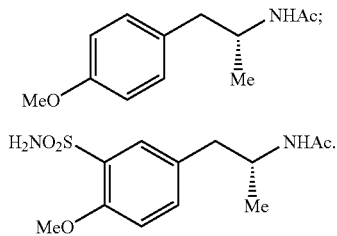

wherein acetamide 5 is represented by the following formula

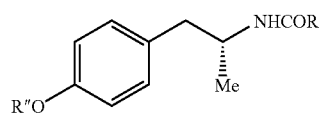

and is prepared using the following intermediates:
(1) (phenol)amido acid 15 having the following formula:

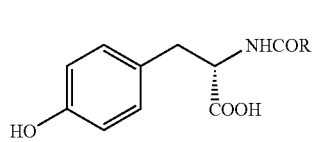

wherein R represents alkyl or aryl, said (phenol)amido acid 15 prepared from a starting material L-tyrosine 7 having the following formula

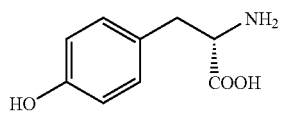

using an acylating agent and a solvent, said acylating agent being selected from the group consisting of RCOX, (RCO)$_2$O and a combination thereof, where X is a halide or a leaving group, where said solvent is selected from the group consisting of alkanes, ethers, DMF, DMSO, ketones, urea and a combination thereof;
(2) (phenol)amidoester 16 having the following formula

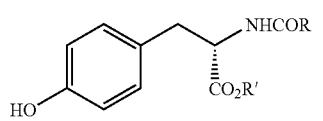

where R and R' represent alkyl or aryl, said (phenol)amidoester 16 prepared from said (phenol)amido acid 15 using an acid chloride and a R'OH, said acid chloride being selected from the group consisting of PCl$_3$, PCl$_5$, POCl$_5$, SOCl$_2$, oxalyl chloride and a combination thereof;
(3) (ether)amidoester 17 having the following formula

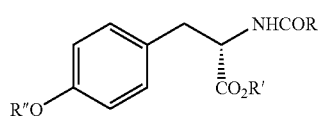

where R, R' and R" represent alkyl or aryl, said (ether) amidoester 17 prepared from said (phenol)amidoester 16 using an alkylating agent a base and a solvent, said alkylating agent being selected from the group consisting of R$_2$SO$_4$, RI, RBr and a combination thereof, said base being selected from the group consisting of amines, carbonates, hydrogen carbonates, amides, alkoxides and a combination thereof; said solvent being selected from the group consisting of H$_2$O, ketones, alkanes, ethers, DMF, DMSO, urea and a combination thereof;
(4) hydroxy(ether)amide 18 having the following formula:

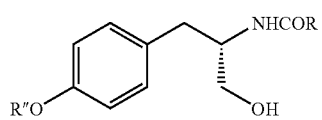

wherein R and R' represent alkyl or aryl, said hydroxy (ether)amide 18 being prepared from said (ether)amidoester 17 using a reducing agent and a solvent, said reducing agent selected from the group consisting of LiAlH$_4$, DIBAL, K-selectride, L-selectride, BH$_3$, NaBH$_4$ and a combination thereof, said solvent being selected from the group consisting of ethers, alcohols, H$_2$O, alkanes, DMF, DMSO, urea and a combination thereof;
said hydroxy(ether)amide 18 used to prepare said acetamide 5 using an acid halide, a solvent an organic acid, MX$_n$ and M, said acid halide being selected from the group consisting of TsCl, MsCl, SOCl$_2$, SO$_2$Cl$_2$, PCl$_3$, PCl$_5$, POCl$_5$, oxalyl chloride and a combination thereof, said solvent being selected from the group consisting of THF, ketones, alkanes, ethers, DMF, DMSO, CH$_2$Cl$_2$, CHCl$_3$, CCl$_4$, urea and a combination thereof, said organic acid being selected from the group consisting of oxalic acid (COOH)$_2$, RCOOH and a combination thereof, where R is H, alkyl, or aryl, said M being selected from the group consisting of Li, Na, K, Mg, Ca, Zn, Pt, Pd, Cu, Co, Mn, Fe, Ni, and Cd, said X being selected from the group consisting of Cl, Br, I, and OAc, and where said n value is 1-3 based on the valence of a metal.

* * * * *